(12) United States Patent
Bosio et al.

(10) Patent No.: US 10,012,647 B2
(45) Date of Patent: Jul. 3, 2018

(54) DEPLETION OF MOUSE CELLS FOR ISOLATION OF HUMAN CELLS

(71) Applicant: Miltenyi Biotec GmbH, Bergisch Gladbach (DE)

(72) Inventors: Andreas Bosio, Cologne (DE); Olaf Hardt, Cologne (DE); David Agorku, Cologne (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 272 days.

(21) Appl. No.: 14/799,942

(22) Filed: Jul. 15, 2015

(65) Prior Publication Data

US 2016/0047808 A1 Feb. 18, 2016

(30) Foreign Application Priority Data

Aug. 14, 2014 (EP) .................................... 14180939

(51) Int. Cl.
*C07K 14/705* (2006.01)
*G01N 33/569* (2006.01)
*C12N 5/00* (2006.01)

(52) U.S. Cl.
CPC ..... *G01N 33/56966* (2013.01); *C07K 14/705* (2013.01); *C12N 5/0081* (2013.01); *G01N 2333/70596* (2013.01)

(58) Field of Classification Search
CPC .......... G01N 33/56966; G01N 33/566; G01N 2333/70596; C07K 14/705; C07K 14/4748; C12N 5/0081
See application file for complete search history.

(56) References Cited

U.S. PATENT DOCUMENTS

| | | | |
|---|---|---|---|
| 2014/0099695 A1* | 4/2014 | Furuta | C12N 1/02 435/180 |
| 2015/0238532 A1* | 8/2015 | Frenette | C12N 5/0663 424/93.7 |

OTHER PUBLICATIONS

Tole et al. Distribution of CD9 in Developing and Mature Rat Nervous System. Developmental Dynamics 197:94-106 (1993).*

* cited by examiner

*Primary Examiner* — Gailene Gabel
(74) *Attorney, Agent, or Firm* — Jaquelin K. Spong

(57) ABSTRACT

A process for depleting host cells from a xenograft of human cells on a murine host is disclosed. The process includes fragmenting the xenograft, subjecting the sample to antibodies specific for a murine CD9 epitope coupled to a detection means, depleting the cell suspension from cells bound by the CD9-antibodies using the detection means, and collecting the cells not bound by the CD9-antibodies as target cells.

6 Claims, 7 Drawing Sheets

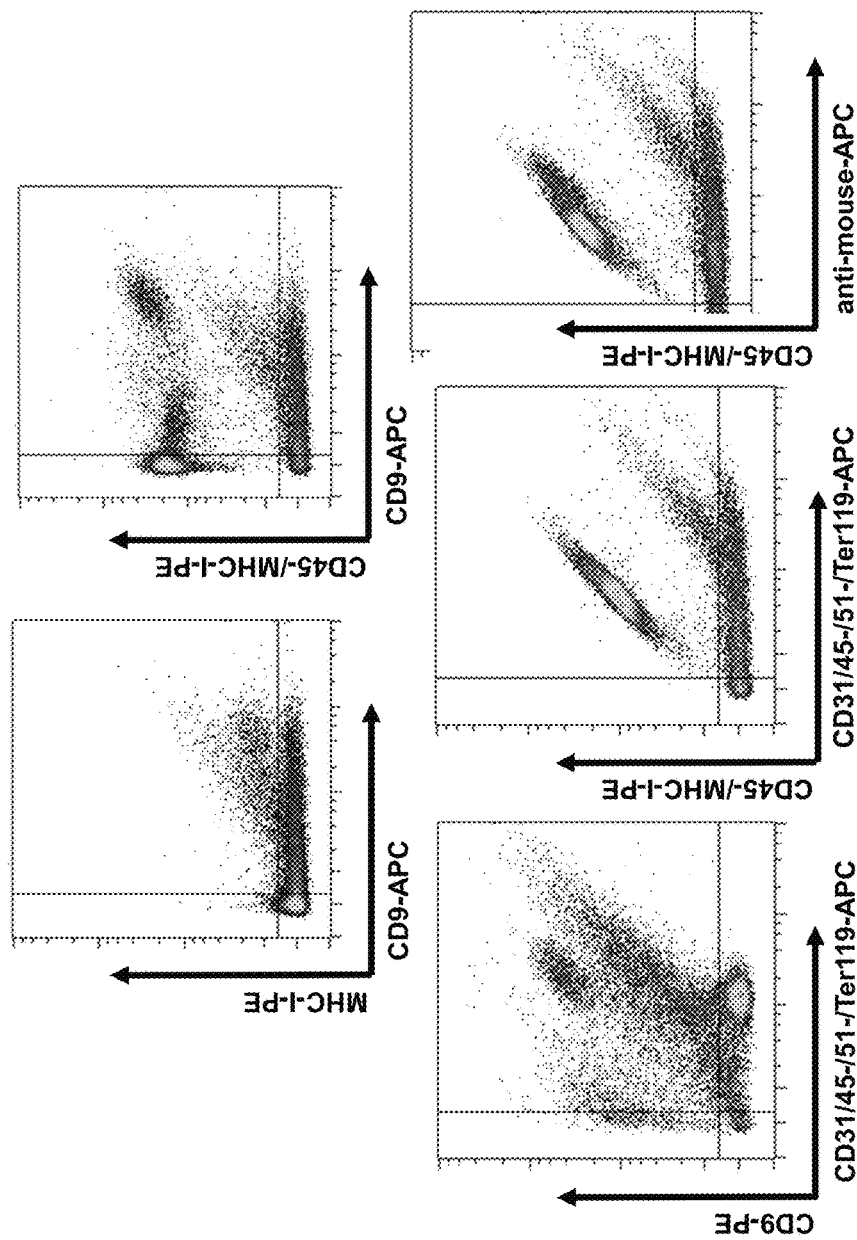
Fig. 4  Lung - Analysis of marker co-expression

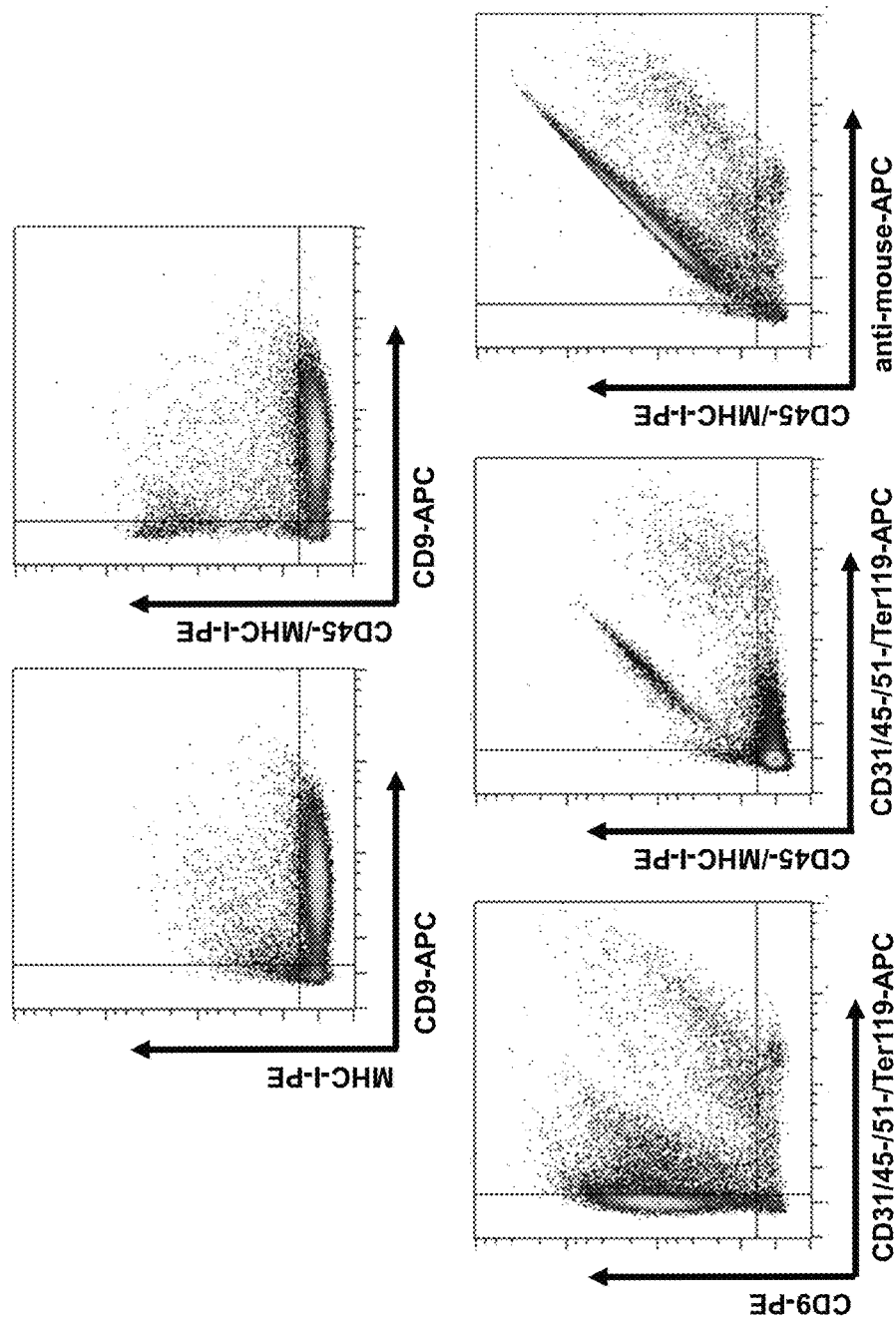
Fig. 5  Skin - Analysis of marker co-expression

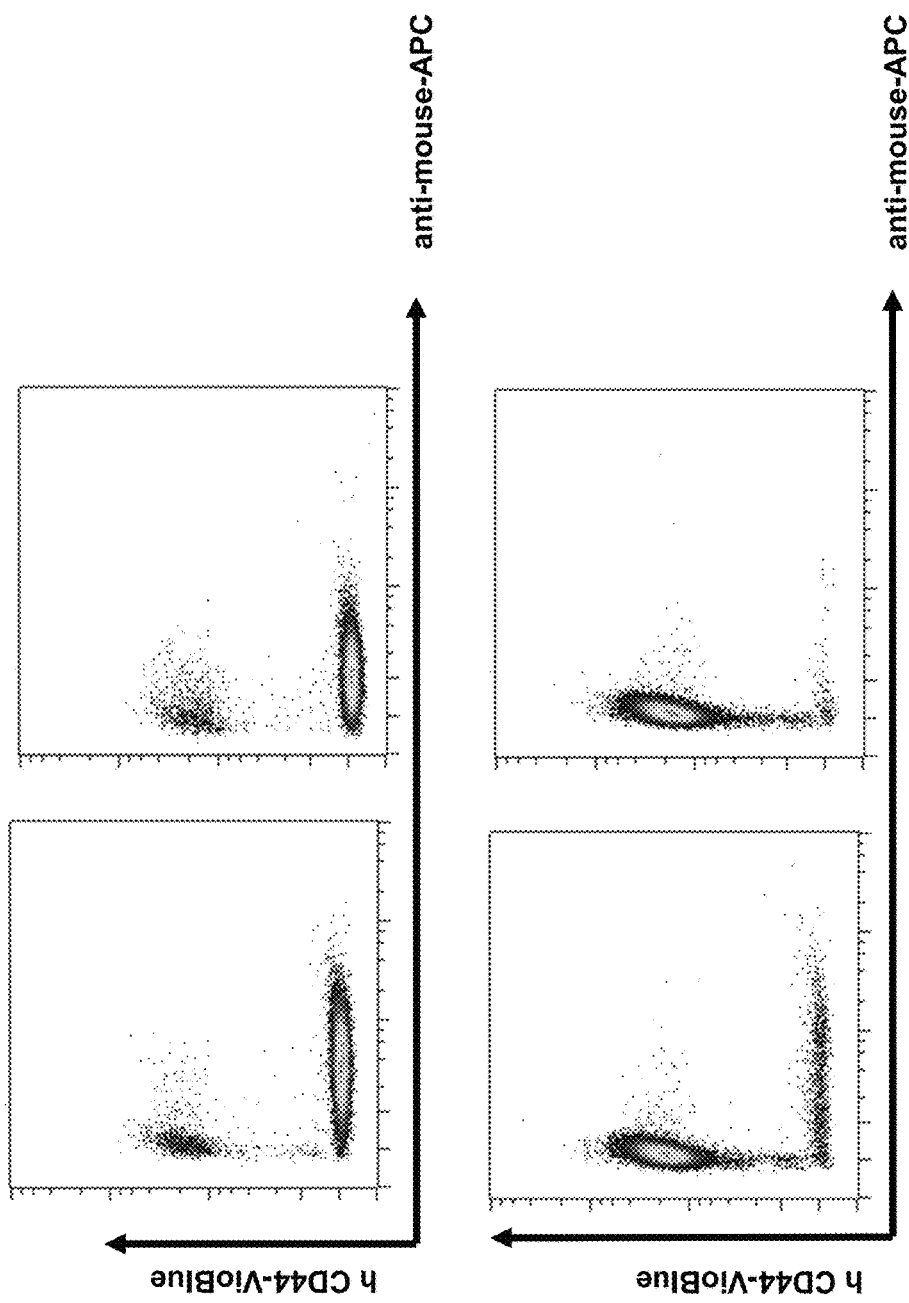
Fig. 6A Brain - Isolation of human glioblastoma cells

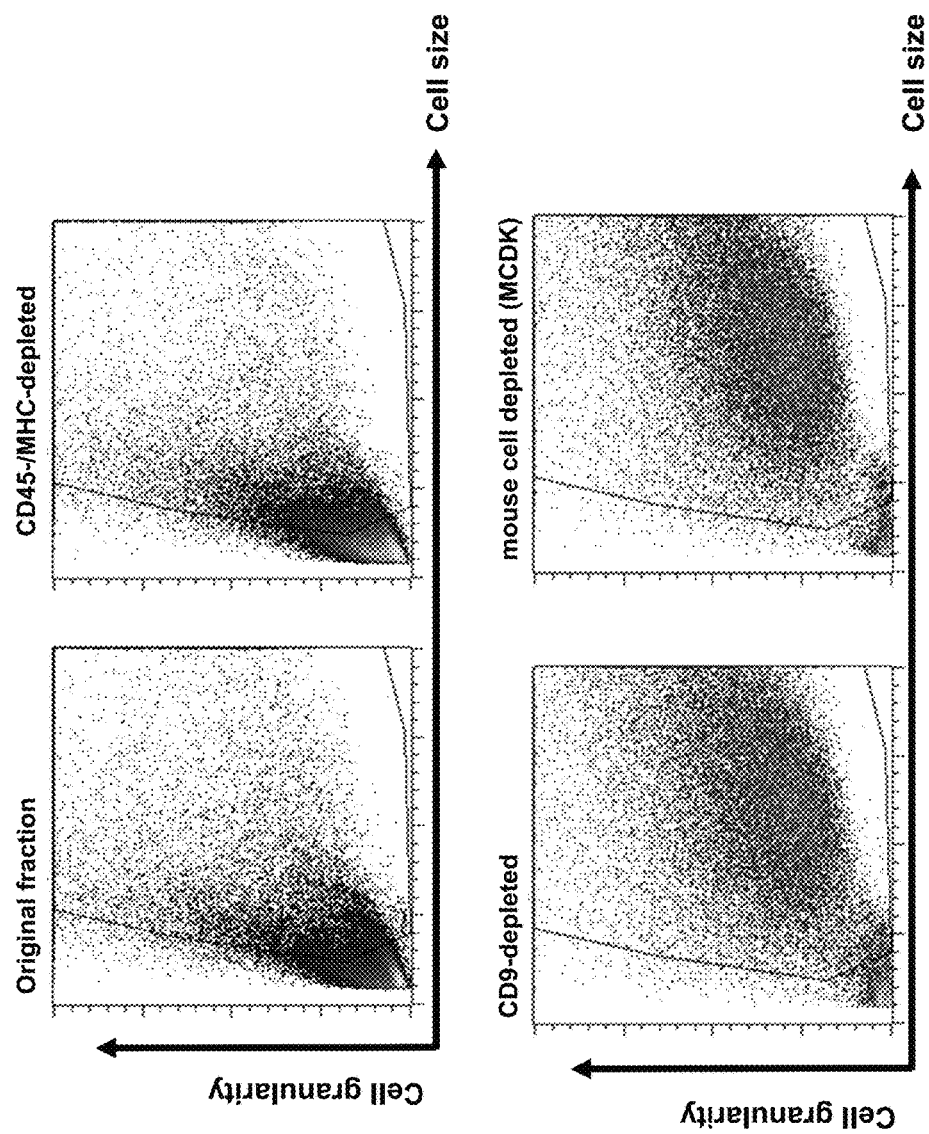
Fig. 6B Brain - Isolation of human glioblastoma cells

DEPLETION OF MOUSE CELLS FOR ISOLATION OF HUMAN CELLS

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

The present invention is directed to the depletion of mouse cells for isolation of human cells.

Human tumor xenografts represent the gold standard method for research areas like drug discovery, cancer stem cell biology, and metastasis prediction. Xenografts can be derived from primary human tumor material, serially transplanted tumor tissue, or cultured cells. When compared to in vitro cell culture models, human tumor xenografts show a higher validity for most assays (Rubio-Viqueira B and Hidalgo, M. (2009) Clin. Pharmacol. Ther. 85: 217-221). Besides its application in cancer research, xenotransplantation of human cells into mice is also frequently used in stem cell research to determine the differentiation potential of a target population.

During the growth phase in vivo, xenografted tissue is vascularized and infiltrated by cells of mouse origin, including heterogeneous lymphocyte subpopulations, fibroblasts, and endothelial cells. The level of infiltration is highly dependent on factors like tumor subtype, growth rate, and region of transplantation. However, even when these factors are kept constant, the amount and composition of infiltrating mouse cells are highly variable, which makes accurate molecular downstream analysis difficult. The contaminating mouse cells lead to cross-hybridization of mouse-derived molecules to human probes on microarrays and/or a significant reduction of sensitivity caused by measurement of mouse signals during next-generation sequencing or proteome analysis (Wong, S. Q. et al. (2013) Sci. Rep. 3: 3494).

In addition, the culture of human tumor cells is frequently hampered by murine fibroblasts overgrowing the target cells. In order to separate mouse cells or fragments of mouse cells from the desired human xenograft, attempts have been made to either deplete the mouse cells or to enhance the analyzing process by software.

In order to deplete mouse cells after xenotransplatation, C. C. Zhang et al. proposed in Stem Cells Transl. Med. 2: 233-242 (2013) combinations of antibodies recognizing mouse CD45 and MHC class I epitopes.

S. B. WILLINGHAM ET AL disclose in PROCEEDINGS OF THE NATIONAL ACADEMY OF SCIENCES, "The CD47-signal regulatory protein alpha (S1RPa) interaction is a therapeutic target for human solid tumors", vol. 109, no. 17, 26 Mar. 2012, pages 6662-6667 the use of antibodies targeted to human epitopes to enrich human cells contaminated by mouse cells. The depletion of mouse cells is not disclosed.

Further combinations of antibodies recognizing mouse cells have been proposed in the prior art, for example WO 2009/045201 A1 discloses the depletion of mouse cells via the murine epitopes CD45, CD31, and H-2K$^{bd}$. Similar, WO 2008/115601 A1 describes mouse MHCI antibodies for depletion of mouse cells. In WO 2012/010904 A1, mouse lineage specific micro-beads are disclosed.

However, using these marker combinations, only a subset of mouse cells can be detected.

Furthermore, the culture of human tumor cells from xenografts is frequently hampered by mouse fibroblasts because the fibroblasts attach and expand more efficiently, thereby overgrowing the target cells. Even when the target cells attach and grow well, in vitro cell culture assays (e.g. drug cytotoxicity testing or pharmakokinetics) are problematic since mathematical correction for effects originating from contaminating mouse cells is impossible in most cases.

Another strategy to isolate human cells from xenografts is to utilize a marker only expressed on human and not on murine cells for depletion of human cells from the xenograft. Thus isolated human cells are bound to a marker which might hamper further purification/selection steps.

SUMMARY

It was an object of the present invention to provide a process to deplete untouched human xenografts from host cells especially from murine cells.

Surprisingly, CD9 was identified as a suitable epitope which allows the detection and depletion of murine cells in a mixture containing murine and human cells.

An object of the invention is therefore a process for depleting host cells from a xenograft of human cells on a murine host characterized in
  a) fragmenting the xenograft into a sample comprising a suspension of single cells
  b) subjecting the sample to antibodies specific for a murine CD9 epitope coupled to a detection means
  c) depleting the sample from cells bound by the CD9-antibodies using the detection means
  d) collecting the cells not bound by the CD9-antibodies as target cells.

The target cells obtained with the process of the invention are preferably substantially "untouched," i.e. substantially not coupled to any antibody.

However, the obtained cells can be coupled after depletion of the host cells to antibodies for further purification.

A vast majority of cell types from the murine host are recognized by CD9 antibodies and can be depleted from the target cells with the process of the invention. Murine cells may be any cells obtainable from rats or mice. This includes murine cells across multiple organs, for example skin, lung, brain, kidney, and skeletal muscle, all of which represent target tissues for xenotransplantation.

The process of the invention is useful to isolate all types of human cells, especially human tumor cells, for example, human breast cancer cells, human colon cancer cells, human lung cancer cells, human prostate cancer cells, human pancreatic cancer cells, human melanoma cancer cells, human leukemia cancer cells, and human lymphoma cancer cells.

A crucial point when using cell surface epitopes for screening is to use a gentle procedure and pure enzymes for tissue dissociation to avoid degradation of the target molecules. Accordingly, in the first step of the process, the xenograft is fragmented or dissociated into a suspension of substantially single cells by mechanical destruction of the tissue with or without the aid of enzymes.

BRIEF DESCRIPTION OF THE DRAWINGS

Various exemplary details are described with reference to the following figures, wherein:

FIG. 4 shows that CD9 was identified as epitope on mouse cells of the lung and even more broad expressed than MHC class I in combination with CD45 on lung tissue;

FIG. 5 shows that CD9 is more broadly expressed than MHC on mouse cells of the skin, even more broadly expressed than MHC class I in combination with CD45; and FIG. 6A shows the isolation of human glioblastoma cells from a mouse brain by depletion of mouse cells by using CD45/MHC I and CD9 for depletion; FIG. 6B shows that next to depletion of viable mouse cells, with CD9-antibodies, dead cells and debris can be removed from the sample, which is not observed when using CD45/MHC for depletion.

DETAILED DESCRIPTION

Figure 1:
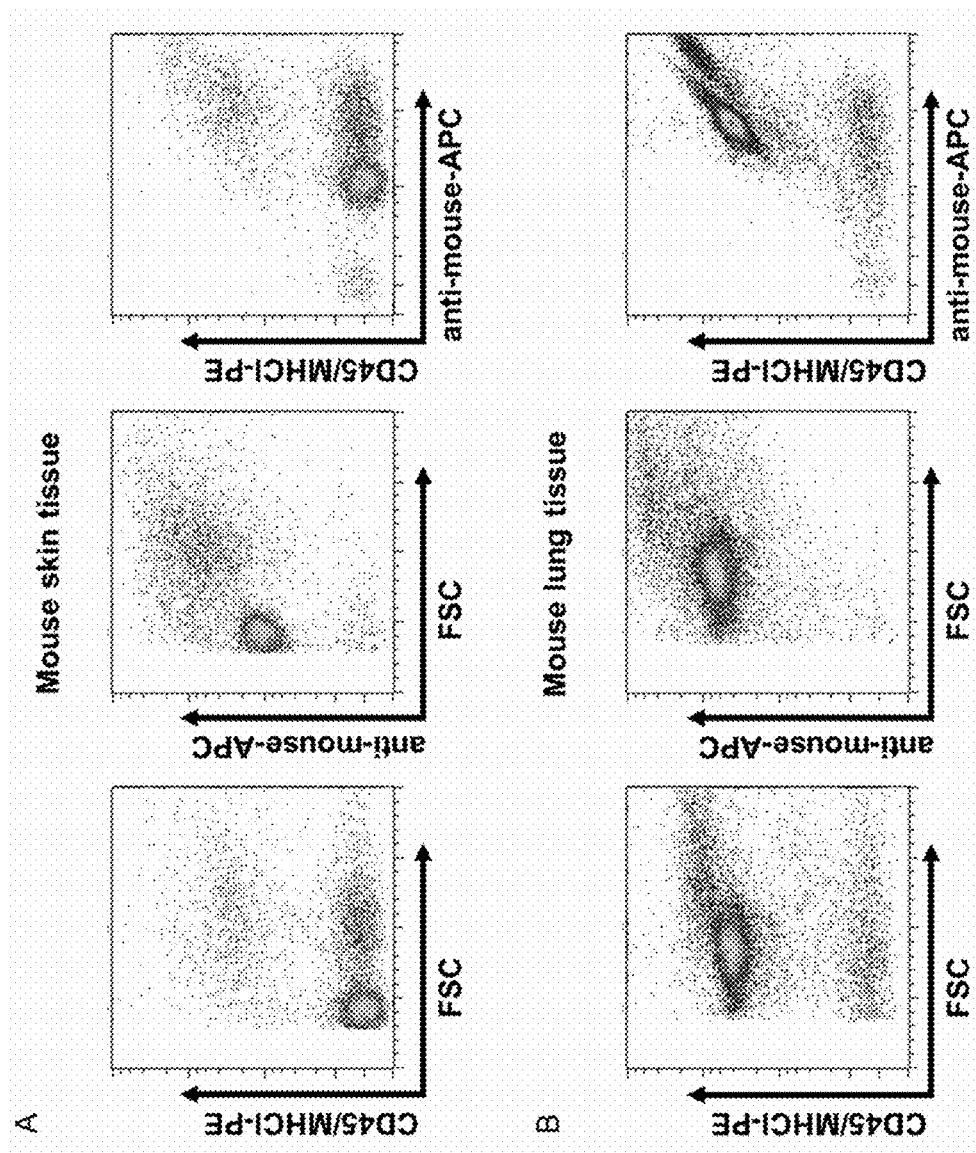
FIG. 1 shows that by a process recognizing murine CD45 and MHC I epitopes, only a subset of mouse cells can be detected; A shows mouse skin tissue; B shows mouse lung tissue.

The term "substantially single cells" means that the tissue is dissociated in isolated, single cells. Dissociation or fragmentation in a fully automated way is for example possible by using the gentleMACS™ Octo Dissociator with heaters and the respective tissue dissociation kits (like Tumor Dissociation Kit human, which is optimized for epitope preservation) both obtainable from Miltenyi Biotec GmbH.

Depending on the desired purity of the target cells, minor fractions of host cells can be removed by adding further antibodies, although for most of those the expression pattern overlaps with CD9.

In another embodiment of the invention, the cell suspension/sample obtained in step a) or step b) or step c) is subjected further to the antibodies specific for a murine CD9 epitope to antibodies specific to one or more murine epitopes selected from the group consisting of CD45, CD51, CD31, CD24, EpCAM, Sca1, CD81, CD44, CD11b, CD95, H2Kk, H2Kd, CD171, CD90.1, CD90.2 and Ter119 each coupled to a detection means. In this embodiment, the xenograft/the cell suspension is depleted from cells coupled to murine CD9 antibody and from cells coupled to these antibodies.

Preferred is the use of an antibody cocktail comprising antibodies specific to the murine epitopes CD9, CD45, CD51, CD31, and Ter119, which is administered in step b) of the process.

The detection means can be the same or different for all antibodies used in the process of the invention. Suitable detection means can be selected from the group consisting of magnetic particles, fluorescent dyes, or a solid support.

Magnetic particles are known in the art as super paramagnetic nanoparticles (Micro Beads), which can be obtained from Miltenyi Biotec GmbH. Suitable fluorescent dyes are for example FITC, PE, APC fluorochromes, or tandem dyes. Solid supports can be plastic dishes or flasks as well as columns or microfluidic elements. Of course, the antibodies may carry one or more detection means.

The depletion of step c) is performed as required by the detection means, for example as magnetic separation, panning, or FACS.

The prior art proposes to isolate certain human tumor subpopulations, such as cancer stem cells (CSCs) from xenografts. However, after a subpopulation has been isolated from the human cell fraction, mouse cells may still contaminate the negative fraction, which leads to biased results in all major types of downstream analysis. Before analyzing the target cells for functional and molecular characteristics, e.g., by microarray-based expression profiling or next-generation sequencing, it is prerequisite to obtain a very pure sample of target cells.

To circumvent this drawback, the process of the invention can be used to yield human cell populations free from contaminating murine host cells. In a further embodiment of the invention, in a step e), the target cells obtained in step d) are subjected to antibodies specific for a human marker coupled to a detection means and further separated using the detection means into at least two fractions comprising distinct cell subpopulations.

Distinct cell subpopulations can consist of cells expressing or not expressing certain markers like CSC or EpCam (CD 326). One fraction obtained in step e) can comprise cell subpopulations expressing these markers, another fraction comprises cell subpopulations not expressing these markers.

In step e) of the invention CSCs can be isolated from, for example, human breast cancer xenograft tumors, human colon cancer xenograft tumors, human lung cancer xenograft tumors, human prostate cancer xenograft tumors, human pancreatic cancer xenograft tumors, human melanoma cancer xenograft tumors, human leukemia cancer xenograft tumors, human lymphoma cancer xenograft tumors.

The overall process involves dissociation of the xenograft for example by using the gentleMACS Octo Dissociator with heaters in combination with the Tumor Dissociation Kit, human, followed by subjecting the sample to the antibodies already discussed and removal of mouse cells in a single step. Subsequently, a second sort was performed using the CSC marker, resulting in pure human CSC and non-CSC subpopulations.

EXAMPLES

Comparative Example 1

Target tissues were removed from BL6 and CD1 mice, pooled, and dissociated in a fully automated way by using the gentleMACS™ Octo Dissociator with Heaters and the respective tissue dissociation kits, which are optimized for epitope preservation. For flow cytometric analysis, cells were stained with the indicated antibodies according to the manufacturer's instructions and analyzed using the MACSQuant™ Analyzer (Miltenyi Biotec GmbH). With the known combinations of antibodies recognizing, mouse CD45 and MHC class I epitopes, only a subset of mouse cells could be detected in all dissociated tissues analyzed as depicted in FIG. 1, 1st column from left, showing skin (A) and lung (B) tissue, even after lysis of red blood cells.

Comparative Example 2

For complete detection of all mouse cells from all organs, antibodies specific for CD45, CD31, CD51 and Ter119 were used in combination with CD9 antibodies as shown by plot C) in FIGS. 4 and 5. Combining these four antibodies with antibodies specific for CD45 and MHC class I is not as efficient as shown by plots D) in FIGS. 4 and 5. Plots E) in FIGS. 4 and 5 point out that the combination of antibodies recognizing CD45, CD31, CD51, Ter119 and CD9 (conforms "anti-mouse") is significantly more efficient for detection of mouse cells than the combination of CD45 and MHC class I antibodies. Moreover, even CD9 alone is already more efficient than the combination of CD45 and MHC class I antibodies.

Comparative Example 3

Human glioblastoma cells were isolated for dissociated mouse brain. As shown in FIG. 6A, the combination of CD45 and MHC class I specific antibodies for indirect magnetic depletion of mouse cells from xenografts is not sufficient. FIG. 6B shows that next to depletion of viable mouse cells, with CD9-antibodies, dead cells and debris can be removed from the sample, which is not observed when using CD45/MHC for depletion.

Identification of CD9 as Marker

The procedure of the comparative example was repeated using antibodies recognizing mouse CD9 instead of CD45 and MHC class I epitopes.

Figure 2:
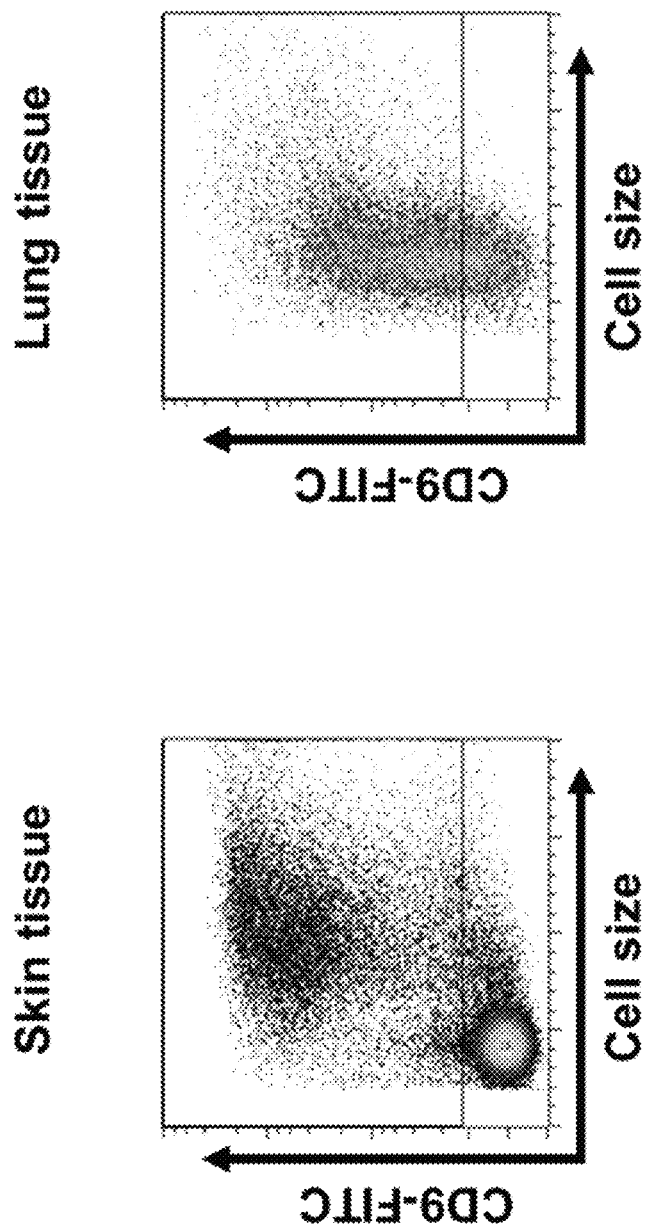
FIG. 2 shows that CD9 is a broadly expressed epitope on murine cells.

CD9 was identified as a broadly expressed epitope on mouse cells allowing for a more general detection as shown in FIG. 2 for dissociated skin and lung tissue. Only red blood cells were not detected in most cases.

For complete detection of all mouse cells from all organs, antibodies specific for mouse CD9, CD45, CD51, CD31, and Ter119 epitopes were added allowing for the binding of all cells by multiple antibodies. Using this antibody composition coupled to APC fluorochromes (Anti-Mouse-APC) it was possible to recognize all cells of mouse origin, including red blood cells, as depicted in FIG. 1, (2. and 3. Column from left), including skin (A) and lung (B) tissue.

Example (1) According to the Invention

Conjugates of anti-mouse CD9, CD45, CD51, CD31 and Ter119 antibodies with superparamagnetic nanoparticles (MicroBeads) were generated as known in the art of antibody coupling on Microbeads. Each antibody was coupled to separate Microbeads and a cocktail of was prepared by mixing the thus obtained conjugates.

The cocktail comprising a mixture of these conjugates was used to develop an optimized protocol for the depletion of mouse cells from human tumor xenografts by magnetic separation. For xenograft tumor generation, female athymic nude mice (Hsd:Athymic Nude-Foxn1$^{nu}$, Harlan), 5-week-old, were maintained under specific pathogen-free conditions. Human cancer xenografts were established from patient's primary tumor surgical specimens, by grafting tumor fragments into the interscapular fat pad of athymic nude mice, and maintained through in vivo passages as previously described (Marangoni E et al., Clin Cancer Res. 2007 Jul. 1; 13(13):3989-98.). Tumor tissue was dissociated into a single cell suspension using the Tumor Dissociation Kit, human in combination with the gentleMACS Octo Dissociator (both Miltenyi Biotec GmbH) according to the manufacturer's instructions. After dissociation, the cells were resuspended in PEB buffer (PBS, pH 7.2, 0.5% bovine serum albumin, and 2 mM EDTA; prepared by diluting MACS BSA Stock Solution 1:20 with autoMACS® Rinsing Solution) for magnetic cell separation.

Figure 3:
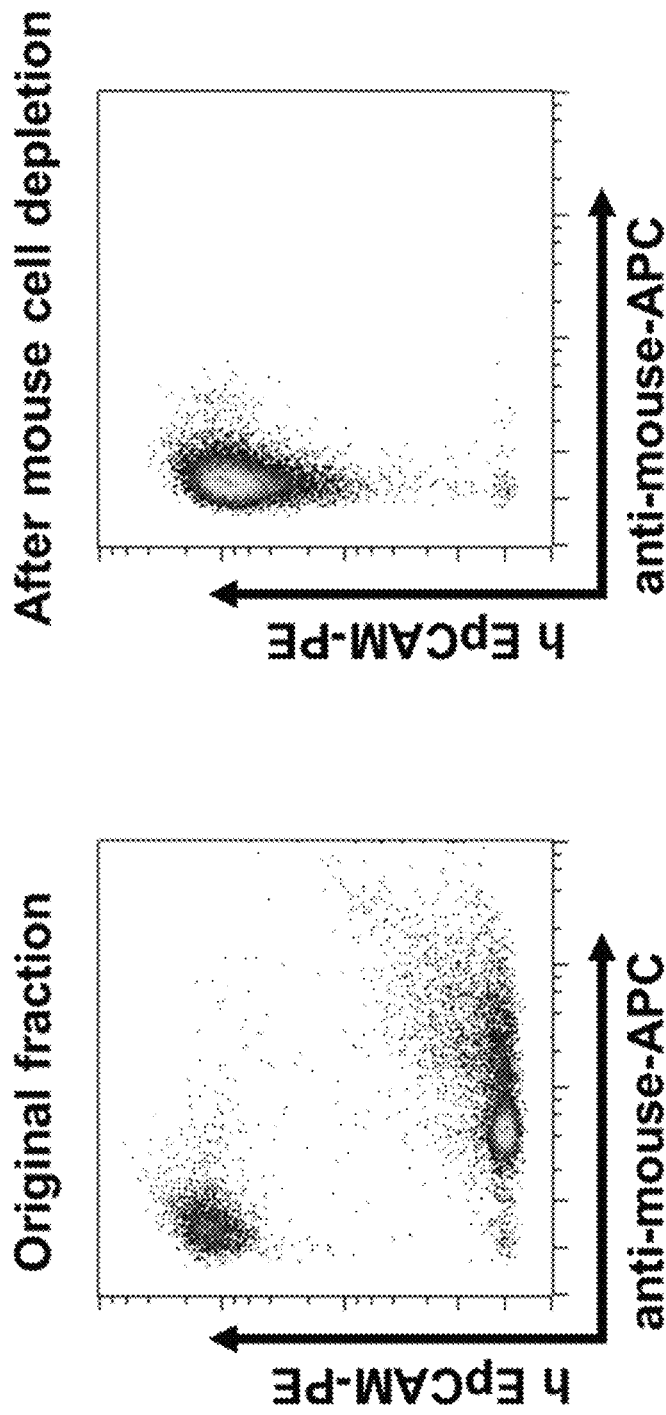
FIG. 3 shows the efficiency of the antibody cocktail according to the invention for elimination of mouse cells in a cell fraction.

Using the conjugate cocktail during step b) of the process of the invention, it was possible to eliminate >99% of the contaminating mouse cells in less than 20 min, even when the frequency of contaminating cells was around 80%, as depicted in FIG. 3. Cell fractions were labeled with the pan-mouse antibody cocktail coupled to APC (anti-mouse-APC) and an antibody against human CD326 (EpCAM) which was used as a marker for human tumor cells in this example allowing for easier quantification of the human and mouse fraction.

Example (2) According to the Invention

The same procedure as described in comparative example 3 was used, In contrast, utilizing CD9 antibodies coupled to MicroBeads is more efficient but does not lead to a highly pure human tumor cell fraction. See FIGS. 6A and B. Surprisingly, by using CD9-Antibodies, dead cells and debris can be efficiently depleted as shown by the plot showing cell size versus cell granularity. With the conjugate cocktail of the invention, it was possible to eliminate >99% of the contaminating mouse cells and >60% of the debris. This effect is not observed when using CD45 and MHC I for depletion.

Therefore, the isolation of human glioblastoma cells from a mouse brain by depletion of mouse cells is inefficient when using CD45 and MHC I for depletion. When using CD9 as depletion marker, the efficiency is significantly improved, however, a small fraction of mouse cells remains in the sample. When using the antibody cocktail according to the invention almost all mouse cells are depleted.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A process for depleting host cells from a xenograft of human cells on a murine host, comprising:
    a) fragmenting the xenograft into a sample comprising a single cell suspension
    b) subjecting the sample to antibodies specific for a murine CD9 epitope coupled to a detection means
    c) depleting the cell suspension from cells bound by the CD9 antibodies using the detection means
    d) collecting the cells not bound by the CD9-antibodies;
    e) subjecting the collected cells not bound by CD9 antibodies obtained in d) to antibodies specific for one or more murine epitopes selected from the group consisting of CD45, CD51, CD31, Ter119, CD24, EpCAM, Sca1, CD11b, CD95, H2Kk, H2Kd, and CD171, each coupled to a detection means, and
    f) depleting the murine cells coupled to these antibodies to obtain human cells.

2. The process according to claim 1, wherein the detection means of the antibodies is selected from the group consisting of magnetic particles, fluorescent dyes, and a solid support.

3. The process according to claim 1, wherein the depletion of step c) is performed as at least one of magnetic separation, panning, and fluorescence activated cell sorting (FACS).

4. The process according to claim 1, wherein mice are used as host.

5. The process according to claim 1, wherein the human cells are human tumor cells.

6. The process according to claim 5 further comprising step g), the human cells obtained in step f) are subjected to antibodies specific for a human marker coupled to a detection means and further separated using the detection means into at least two fractions comprising distinct cell subpopulations.

* * * * *